(12) United States Patent
Gorbunov

(10) Patent No.: US 8,109,129 B2
(45) Date of Patent: Feb. 7, 2012

(54) PORTABLE NANOPARTICLE SIZE CLASSIFIER

(75) Inventor: Boris Zachar Gorbunov, Canterbury (GB)

(73) Assignee: Naneum Limited, Kent (GB)

( * ) Notice: Subject to any disclaimer, the term of this patent is extended or adjusted under 35 U.S.C. 154(b) by 421 days.

(21) Appl. No.: 11/994,081

(22) PCT Filed: Jun. 29, 2006

(86) PCT No.: PCT/GB2006/002391
§ 371 (c)(1),
(2), (4) Date: Apr. 4, 2008

(87) PCT Pub. No.: WO2007/000602
PCT Pub. Date: Jan. 4, 2007

(65) Prior Publication Data
US 2008/0196484 A1    Aug. 21, 2008

(30) Foreign Application Priority Data
Jun. 29, 2005 (GB) .................................. 0513358.2

(51) Int. Cl.
*G01N 1/00* (2006.01)
*G01N 1/24* (2006.01)
(52) U.S. Cl. .................................... 73/28.04; 73/863.03
(58) Field of Classification Search ................. 73/28.04, 73/28.01, 863.03
See application file for complete search history.

(56) References Cited

U.S. PATENT DOCUMENTS

| 4,463,595 A | * | 8/1984 | Yeh et al. | 73/28.01 |
| 5,932,795 A | | 8/1999 | Koutrakis et al. | |
| 5,983,704 A | * | 11/1999 | Park et al. | 73/28.01 |
| 6,033,459 A | * | 3/2000 | Hase | 95/82 |
| 2004/0151672 A1 | | 8/2004 | Yoshida et al. | |

FOREIGN PATENT DOCUMENTS

| CH | 693491 A5 * | 8/2003 |
| GB | 2347879 A | 9/2000 |

OTHER PUBLICATIONS

Feldpausch, et al., "Measurement of Ultrafine Aerosol Size Distribution by a Combination of Diffusion Screen Separators and Condensation Particle Counters," Journal of Aerosol Science, vol. 37, No. 5, May 2006, pp. 577-597.*

(Continued)

*Primary Examiner* — Hezron E Williams
*Assistant Examiner* — Nathaniel Kolb
(74) *Attorney, Agent, or Firm* — Heslin Rothenberg Farley & Mesiti P.C.

(57) ABSTRACT

A nanoparticle size classifier comprising a variable flow rate system with a single diffusion element 3 placed inside a cell 2 containing inlet 1 and outlets 6 and 7, an aerosol filter 8, flow meter 9, pump 10 and pump controller 11, which enables a plurality of measurements to be obtained by means of passing an aerosol through the diffusion element 3 at various flow rates. Preferably, outlet of the diffusion cell is connected to a particle counter 5 via a three-way valve 6. The diffusion element has a net or screen that permit air through but capture some particles. In a preferred embodiment, the nanoparticle size classifier is connected to a PC 12 (a notebook or a palm-size computer) to acquire and process data.

20 Claims, 1 Drawing Sheet

OTHER PUBLICATIONS

Feldspausch, et al. "Measurement of Ultrafine Aerosol Size Distribution by a Combination of Diffusion Screen Separators and Condensation Particle Counters," Journal of Aerosol Science, vol. 37, No. 5, May 2006, pp. 577-597.*

Feldspausch, et al. "Measurement of Ultrafine Aerosol Size Distribution by a Combination of Diffusion Screen Separators and Condensation Particle Counters," Journal of Aerosol Science, vol. 37, No. 5, May 2006, pp. 577-597.*

Seol, et al.. "A differential mobility analyzer with adjustable column length for wide particle-size-range measurements," Journal of Aerosol Science, vol. 33, Jun. 2002, pp. 1481-1492.*

Feldpausch, et al., "Measurement of Ultrafine Aerosol Size Distributions by a Combination of Diffusion Screen Separators and Condensation Particle Counters," Journal of Aerosol Science, vol. 37, No. 5, May 2006, pp. 577-597.

International Search Report for PCT Appln. PCT/GB2006/002391 dated Oct. 6, 2006.

Written Opinion of ISR for PCT Appln. PCT/GB2006/002391.

* cited by examiner

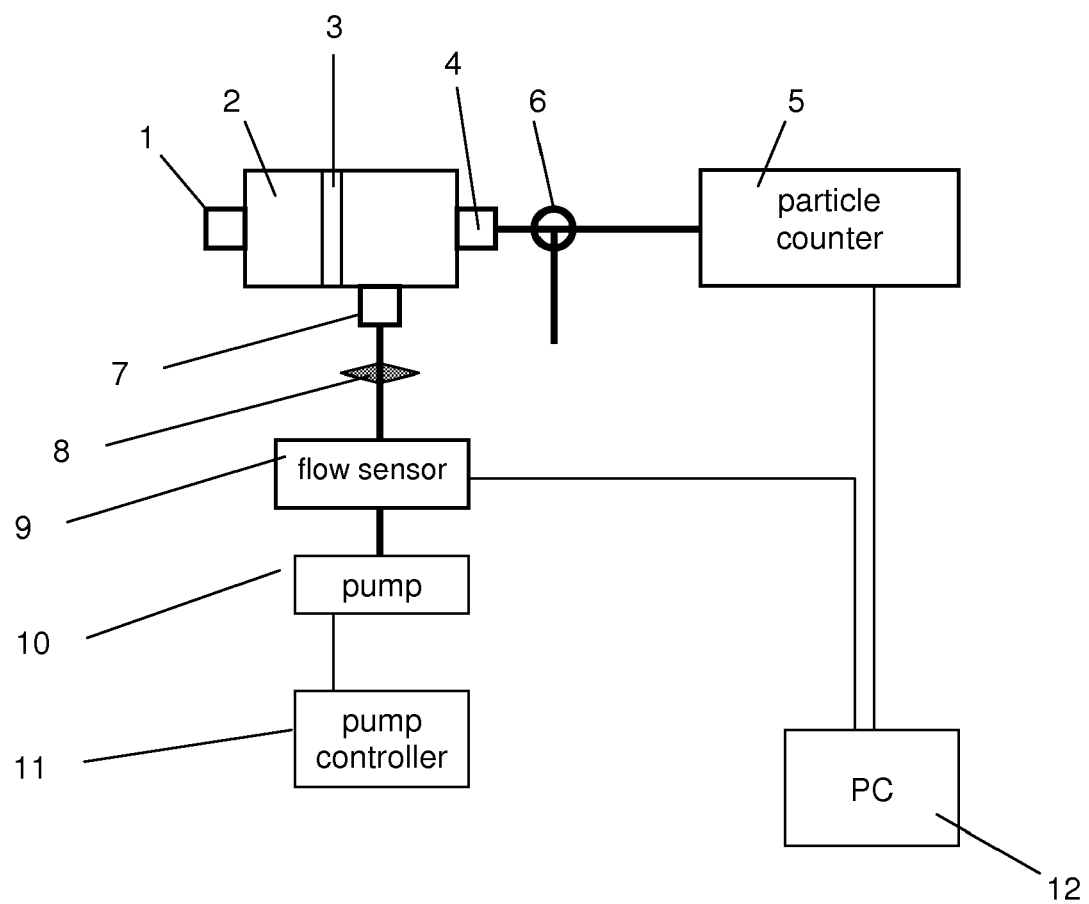

PORTABLE NANOPARTICLE SIZE CLASSIFIER

CROSS-REFERENCE TO RELATED APPLICATIONS

This application is a §371 filing of PCT application PCT/GB2006/002391 filed on Jun. 29, 2006 which claims priority from British application 0513358.2 filed on Jun. 29, 2005. The disclosures of these applications are included by reference herein in their entirety.

BACKGROUND OF THE INVENTION

1. Field of the Invention

This invention relates to airborne nanoparticle size classification for purposes of characterisation of the number concentration of particles in various size ranges using portable and hand-held means.

2. Description of Related Art

The motion of nanoparticles in a gas medium is influenced by diffusion. A particle undergoing diffusion travels a random, irregular path. Its position at any given time depends on the carrier gas movement and most recent collisions with molecules of the gas. Smaller particles with less momentum are more strongly affected than larger particles with greater inertia. Sub-micron and larger particles are not significantly affected by diffusion at normal temperatures and pressures. As particles undergoing diffusion pass through a fine mesh screen, some collide with the screen wires. Surface-attractive forces between particle and wire cause the particle to stick to the surface of screens. Because of diffusion, a larger fraction of small particles will collide with the screen than will large particles. Thus, the penetration of small particles will be lower than for large particles.

It is important to recognise that the nanoparticles are much smaller than the mesh opening size of the screen (normally about 20 micrometers). Therefore, the usual screen collection method for large particles, interception used in the life science and technology, is not applicable. The screen-type Diffusion Battery usually consists of ten stages. Each stage contains one or more screens. For the Model 3040 (see for instance: Model 3040/3041 Diffusion Battery Instruction Manual, TSI, St. Paul, Minn.), the first stage contains one screen, the second contains two screens, the third contains three screens, and so on. The first stage removes a large fraction of the smallest particles but allows nearly all 0.1-micrometer ($\square$m) particles to penetrate. Each successive stage removes a larger fraction of the larger particles. Finally, by the time the aerosol has passed all ten stages, a significant fraction of the 0.1-micrometer particles have been removed.

A diffusion battery is a convenient instrument for characterising airborne nanoparticles or aerosol particles. The Model 3040/3041 Diffusion Battery classifies aerosol particles according to size in the diameter range of 2 nm to 0.2 micrometers. It has ten stages of classification and 11 sampling ports: one at the entrance and one behind each of the ten stages. Each stage consists of one or more fine mesh stainless-steel screens (the multiple screens are in series with each other). The first stage, with one screen, removes about 50 percent of the 0.006-micrometer diameter particles from the aerosol stream at a flow rate of 4 liters per minute. Aerosol that penetrates the two screens of the second stage—making a total of three screens from the entrance—has already had about 50 percent of the 0.018-micrometer particles removed. Aerosol that penetrates the ninth stage (with nine screens), making a total of 45 screens from the entrance, has had about 50 percent of the 0.20-micrometer particles removed.

The Diffusion Battery is normally used as a particle size classifier. It is typically placed upstream of an aerosol concentration detector such as a Condensation Particle Counter (CPC). The detector is first connected to the sample port upstream of the first stage of the Diffusion Battery, then downstream of the first stage, then downstream of the second stage, and so on. Since fractional aerosol penetration depends upon the size of aerosol particles, the size distribution from the particle penetration data may be evaluated. Thus, particle size distribution is determined from stage-penetration data.

The Diffusion Battery can be used with TSI's Model 3022A continuous-flow Condensation Particle Counter or Model 3025A Ultrafine Condensation Particle Counter or with any other particle detecting instrument. An automatic port selector (Model 3042 Automatic Switching Valve) is used with the Diffusion Battery and the CPC enables the flow to be directed through various stages.

A diffusion battery is a large, heavy, desktop instrument that cannot be readily employed outdoors or at a live factory. This is because a diffusion battery requires a complicated flow maintenance system (e.g. an Automatic Switching Valve) that enables the aerosol flow to be passed through different stages of a battery. In U.S. Pat. No. 4,463,595 authors suggest to use a seven-cell, parallel flow, screen-type diffusion battery for the size characterisation and size classification of ultra-fine aerosols. The parallel flow diffusion battery comprises an intake manifold for receiving an aerosol and distributing it to a plurality of diffusion cells extending through a cell holding surface. Each cell has a tubular body extending through the surface and means for diffusing an aerosol and a filter serially mounted within the tube. The density of each diffusing means differs from the density of the diffusing means for each other cell, permitting a plurality of measurements to be simultaneously taken from each aerosol sample. In a preferred embodiment, the diffusing means comprises a number of wire screens, the number of screens being different within each cell. This invention enables aerosols to be characterised without complex flow distributing system. However, aerosol filters are used in the invention to collect particles for further analysis, for instance using gravimetric technique. Therefore, it cannot be employed for on-line in situ characterisation of aerosol particles and it cannot be coupled with a single particle counter.

The particle number concentration decreases continuously as it goes through the successive diffusion elements (screens/nets) due to increase in the time particles are in the vicinity of wires of screens. In practice, concentration measurements are taken as a function of number of screens. They contain information about particle size distributions. It is important for the current invention that, in principle, the plurality of measurements can be obtained in another way (using a single screen) by means of changing the flow rate of the carrier gas containing particles. The lower flow rate the more time particles are in the vicinity of wires and the greater fraction of the particles are removed from the flow. Therefore, concentration measurements obtained at various flow rates contain similar information regarding particle size distributions as measurements with different number of screens in a conventional diffusion battery.

SUMMARY OF THE INVENTION

It is an object of this invention to provide a nanoparticle size classifier comprising a variable flow rate system with a single diffusion element placed inside a cell containing inlet and outlet, flow meter, pump and pump controller, which enables a plurality of particle number concentration measurements to be obtained by means of passing an aerosol through the diffusion element at various flow rates.

Additional objects, advantages and novel features of this invention will become apparent to those skilled in the art upon examination of the following description or may be learned by practice of the invention.

To achieve the foregoing and other objects and in accordance with the purpose of the present invention, as embodied and broadly described herein, the nanoparticle size classifier of this invention may comprise an inlet for receiving an aerosol, a diffusion element positioned across the aerosol flow in a diffusion cell, outlet of the diffusion cell connected to a particle counter, another outlet sequentially connected to an aerosol filter, a flow meter, a pump controlled by a controlling device that includes an electric battery and a three way valve positioned between the first outlet and the particle detector. The diffusion element has a net or screen with wires that permit air through but capture some particles. The particle detector may be a condensation particle counter. In a preferred embodiment, the nanoparticle size classifier is connected to a condensation particle counter and a PC (a notebook or a palm-size computer) to collect and process data.

BRIEF DESCRIPTION OF THE DRAWINGS

The accompanying drawings, which are incorporated in and form a part of the specification, illustrate an embodiment of the present invention and, together with the description, serve to explain the principles of the invention.

FIG. 1 is a schematic of the invention, showing the connections to a PC.

DETAILED DESCRIPTION OF THE INVENTION

FIG. 1 shows a schematic of a nanoparticle size classifier connected to a PC and a condensation particle counter in accordance with the preferred embodiment of this invention. The nanoparticle size classifier includes an inlet 1 of an aerosol, attached to a diffusion cell 2, containing diffusion element 3, the first outlet 4 connected to a particle counter 5 via a three way valve 6, the second outlet 7 sequentially connected to an aerosol filter 8, a flow sensor 9, a pump 10, a pump controller 11 with an electric battery. The particle counter and 5 and flow sensor 9 are connected to a PC 12. In accordance with this invention, it should be understood that various PCs or other means of data acquisition could be employed to store and to process data.

The principle of operation is as follows. At the beginning the three-way valve 6 is in the position when it connects the particle counter 5 with the first outlet 4. Aerosol particles enter the diffusion cell 2 through the inlet 1. In the cell some particles are captured by the diffusion element 3. The flow at the first outlet 4, therefore, contains lesser particles than the flow in the inlet 1. The number concentration of aerosol particles coming out of the outlet 4 (N) is measured then by means of a particle counter 5 and recorded by the PC 12. The particle counter counts continuously. The number of particles captured by the diffusion element 3 is influenced by the flow rate through it. The penetration of aerosol particles through net or screen type diffusion element is described in U.S. Pat. No. 4,463,595 (the disclosure in which is incorporated herein by reference) and many other publications. The total flow rate through the element 3 is the sum of the variable flow rate ($Q_v$) generated by the pump 10 and the constant flow rate through the CPC (0.7 l/min). The variable flow rate is controlled by the pump 10 and recorded by the flow sensor 9. Thus, the first couple of measurements ($N_1$ and $Q_1$) are recorded. Here $Q_1=Q_v+0.7$ l/min. After completing the first measurements the pump controller 11 changes the flow rate of the pump 10 and the number concentration of aerosol particles is measured again by the particle counter 5 and recorded by the PC 12. This provides the second pair of measurements ($N_2$ and $Q_2$). In the same way several more pairs of measurements are obtained. The total number of measurements depends upon the accuracy and resolution required and can be vary from just one up to 10 or 20 or as many as practical to obtain the size distribution. Finally, the three-way valve 6 is turned into the position when it connects the particle counter 5 with the open air and the concentration of the particles in the air is measured and recorded $N_0$. This will be the same concentration as the concentration at the inlet 1 of the diffusion cell 2. In the PC the penetration efficiencies $E_i$ will be calculated from the concentrations measured: $E_i=N_i/N_0$. The set of measurements described above ($E_i$ and $Q_i$) is sufficient to restore the aerosol particle size distribution as it.

A description of the technique for aerosol particle size distribution reconstruction may be found in many publications, e.g. in an article by YEH HSU-CHI and CHENG YUNG-SUNG (1980) "Theory of a Screen-Type Diffusion Battery", J. AEROSOL SCI., Vol. 11, pp. 313-320, the disclosure in which is incorporated herein by reference. The use of the technique described there will become apparent to those skilled in the art upon examination.

The set of penetration efficiencies $E_i$ provides similar information as the set of penetration efficiencies measured with the conventional diffusion battery. The difference is that instead of taking measurements at the same flow rate but various numbers of screens we are using the only diffusion element and various flow rates. The later provides many advantages: lower dimensions, simple flow arrangement, lower weight, lower costs of manufacturing and more flexibility because it is easier to change the flow rate in our apparatus than to change the number of diffusion elements in a diffusion battery.

A portable aerosol spectrometer have been built using Hand-held CPC 3007 (TSI, USA) as a particle counter, air flow sensor (Honeywell), pump control and micro pump G 6/04 (Rietschle Thomas, UK). The diffusion cell was manufactured from aluminium to house 47 mm diameter Nylon nets with mesh opening 410 m (Millipore). The spectrometer is powered by a 9V battery. The CPC has its own battery power source.

An example of the penetration efficiency data is shown in Table 1.

| Total flow rate $Q_i$, L/min | E |
| --- | --- |
| 4.5 | 0.80 |
| 4.1 | 0.78 |
| 3.6 | 0.75 |
| 3.2 | 0.71 |
| 2.8 | 0.66 |
| 2.5 | 0.62 |
| 2.1 | 0.54 |
| 1.7 | 0.38 |
| 1.4 | 0.25 |
| 0.8 | 0.08 |

The tests of the novel apparatus have been performed using an aerosol of W obtained with photochemical aerosol generator with modal diameter $\square_m$=25 nm and $\square_g$=1.3. The aerosol was characterised with a conventional diffusion battery that was used as a reference method. It was found that the novel aerosol spectrometer provides data in a good agreement with the reference method: $D_m$=23.5±15 nm and $\square_g$=1.35±0.05 were found (5 runs).

The particular components and equipment discussed above are cited merely to illustrate a particular embodiment of the invention. It is contemplated that the use of this invention may involve different components as long as the principle, utilising a variable flow rate through a diffusion element, is followed. A portable nanoparticle size classifier so constructed will provide a sensitive, reliable means of the classification of size of nanoparticles for obtaining aerosol size distributions. It is intended that the scope of the invention be defined by the claims appended hereto.

In practice, a wider flow range can be used to increase the range of nanoparticles to be characterised. Another way of increasing the resolution and the accuracy of measurements is an increase the number of measurements within the flow rate range. If the pump is controlled by a PC or another re-programmable device then this can be achieved automatically depending on the reading of the particle detector.

The invention claimed is:

1. A nanoparticle size classifier comprising a variable flow rate system, wherein the variable flow rate system comprises:

a diffusion cell having a single diffusion element disposed therein, the diffusion cell having an inlet and an outlet;

a flow meter;

a pump; and a pump controller for controlling variable flow rates within the variable flow rate system;

wherein the variable flow rate system is arranged to enable a plurality of particle number concentration measurements to be obtained by passing an aerosol through the diffusion element at various flow rates.

2. The nanoparticle size classifier of claim 1, wherein said single diffusion element comprises one of a single net filter and a screen placed inside the diffusion cell.

3. The nanoparticle size classifier of claim 2, wherein two or more pumps are connected to increase the range of the flow rates.

4. The nanoparticle size classifier of claim 2, wherein a T-connector is used to connect the pump and a particle detector to the diffusion cell.

5. The nanoparticle size classifier of claim 2, wherein the classifier further comprises a three way valve operatively connected between a particle detector and the diffusion cell to enable said particle detector to directly measure a particle number concentration in a gas medium entering the inlet of the diffusion cell.

6. The nanoparticle size classifier of claim 1, wherein said single diffusion element comprises one of a pack of net filters and a pack of screens placed within the diffusion cell.

7. The nanoparticle size classifier of claim 6, wherein two or more pumps are connected to increase the range of the flow rates.

8. The nanoparticle size classifier of claim 6, wherein a T-connector is used to connect the pump and a particle detector to the diffusion cell.

9. The nanoparticle size classifier of claim 6, wherein the classifier further comprises a three way valve operatively connected between the particle detector and the diffusion cell to enable said particle detector to directly measure a particle number concentration in a gas medium entering the inlet of the diffusion cell.

10. The nanoparticle size classifier of claim 1, wherein two or more pumps are connected to increase the range of the flow rates.

11. The nanoparticle size classifier of claim 10, wherein a T-connector is used to connect the pump and a particle detector to the diffusion cell.

12. The nanoparticle size classifier of claim 10, wherein the classifier further comprises a three way valve operatively connected between a particle detector and the diffusion cell to enable said particle detector to directly measure a particle number concentration in a gas medium entering the inlet of the diffusion cell.

13. The nanoparticle size classifier of claim 1, wherein a T-connector is used to connect the pump and a particle detector to the diffusion cell.

14. The nanoparticle size classifier of claim 13, wherein the classifier further comprises a three way valve operatively connected between a particle detector and the diffusion cell to enable said particle detector to directly measure a particle number concentration in a gas medium entering the inlet of the diffusion cell.

15. The nanoparticle size classifier of claim 1, wherein the classifier further comprises a three way valve operatively connected between a particle detector and the diffusion cell to enable said particle detector to directly measure a particle number concentration in a gas medium entering the inlet of the diffusion cell.

16. The nanoparticle size classifier of claim 1, wherein the diffusion cell inlet is adapted to receive the aerosol;

wherein the single diffusion element is positioned across a flow of the aerosol in the diffusion cell;

wherein the diffusion cell outlet comprises a first outlet operatively connected to a particle counter;

wherein the classifier further comprises a three way valve operatively connected between the first outlet and the particle counter; and wherein the diffusion cell further comprises a second outlet, the second outlet sequentially connected to an aerosol filter, the flow meter, and the pump, wherein the pump is adapted to be controlled by the pump controller and provide the various flow rates.

17. The nanoparticle size classifier according to claim 16, wherein the particle counter is a condensation particle counter.

18. A nanoparticle size classifier according to claim 16, wherein the classifier is connected to a condensation particle counter and a PC adapted to collect and process data from the classifier.

19. A method of nanoparticle size classification using the apparatus of claim 1, the method comprising:

passing the aerosol through the single diffusion element of the apparatus at the various flow rates;

obtaining the plurality of particle number concentration measurements ($N_i$) coming out of the outlet of the diffusion cell at the various flow rates;

measuring the number ($N_0$) of particles in air entering the inlet of the diffusion cell; and calculating a penetration efficiency ($E_i$) at each of the various flow rates from the relationship $E_i=N_i/N_0$ to provide a nanoparticle size classification.

20. The method of nanoparticle size classification of claim 19, wherein said single diffusion element comprises one of a pack of net filters and a pack of screens placed within the diffusion cell.

* * * * *